United States Patent [19]

Fujimoto et al.

[11] 4,235,812

[45] Nov. 25, 1980

[54] PROCESS FOR PREPARING THIOUREA DIOXIDE

[75] Inventors: Osamu Fujimoto; Jiro Watanabe; Kazuyoshi Kushibe, all of Fuji, Japan

[73] Assignee: Tokai Denka Kogyo Kabushiki Kaisha, Tokyo, Japan

[21] Appl. No.: 55,789

[22] Filed: Jul. 9, 1979

[30] Foreign Application Priority Data

Jul. 25, 1978 [JP] Japan ................................ 53-89986

[51] Int. Cl.$^3$ .......................................... C07C 145/00
[52] U.S. Cl. ................................................ 260/513.7
[58] Field of Search ...................................... 260/513.7

[56] References Cited

U.S. PATENT DOCUMENTS

| 2,150,921 | 3/1939 | Havas | 260/513.7 |
| 2,347,446 | 4/1944 | Walker | 260/513.7 |
| 2,783,272 | 2/1957 | Young | 260/513.7 |

FOREIGN PATENT DOCUMENTS

| 45-17665 | 6/1970 | Japan | 260/513.7 |
| 50-62934 | 5/1975 | Japan | 260/513.7 |

Primary Examiner—Nicky Chan
Attorney, Agent, or Firm—Scully, Scott, Murphy & Presser

[57] ABSTRACT

According to this invention there is provided a process for preparing thiourea dioxide characterized in that in the production of thiourea dioxide by the reaction of thiourea and hydrogen peroxide in an aqueous solvent, ammonium bicarbonate is added to the reaction solution at a proper time.

5 Claims, No Drawings

PROCESS FOR PREPARING THIOUREA DIOXIDE

BACKGROUND OF THE INVENTION

1. Field of the Invention

This invention relates to a process for preparing thiourea dioxide (hereinafter referred to as "T.U.D.") and more particularly to an improved process for preparing T.U.D. in high yield and high purity in the production of T.U.D. by the reaction of thiourea and hydrogen peroxide.

2. Description of the Prior Art

The production of T.U.D. by the reaction of thiourea and hydrogen peroxide is already well known, and various methods have been proposed to improve the reaction yield and obtain products of high purity. For example, maintaining the reaction temperature in a certain range, improving the method of feeding thiourea and hydrogen peroxide, controlling the molar ratio of thiourea to hydrogen peroxide in the reaction solution, maintaining the pH of the reaction solution neutral or weak acid, etc. Thus, mainly known are methods of preventing the production of side reaction substances during reaction and suppressing the decomposition of T.U.D. However, all these methods are unsatisfactory as the method of preventing the production of by-products during reaction and suppressing the decomposition of T.U.D., and they afford only low yield and low purity of the object product, and a satisfactory result has not been obtained.

Solvents used in these methods can be broadly classified into non-aqueous and aqueous solvents.

The method of preparing T.U.D. by the reaction of thiourea and hydrogen peroxide in a non-aqueous solvent (chlorinated solvents such as carbon tetrachloride and chloroform, as well as lower aliphatic alcohols) has been proposed by German Pat. No. 917553, Italian Pat. No. 579119 and French Pat. No. 2040797. According to the said method, T.U.D. as the reaction product does not dissolve in the solvent, so that all the T.U.D. produced can be recovered as product. However, despite such an advantage, the quantity of by-products is large because the reaction of thiourea and hydrogen peroxide is a heterogeneous reaction. Besides, such by-products are incorporated into the product T.U.D. since they do not dissolve in the solvent, thus causing the purity of the product to deteriorate. Furthermore, there is the loss of solvent used. Because of these demerits, an industrial adoption of the said method is disadvantageous.

On the other hand, the production of T.U.D. in an aqueous solvent is advantageous in that since the starting thiourea dissolves well in water and forms a homogeneous phase, the quantity of by-products is small and a relatively high purity T.U.D. is obtained. Because of such a merit, this method is mainly adopted at present, and studies are being made about the improvement of this method.

U.S. Pat. No. 2,783,272 proposes maintaining the pH of the reaction solution at 2 to 6 as the method of improving the yield and purity of product. According to the said U.S. patent, at pH values below 2 of the reaction solution, T.U.D. is not produced with formation of only disulfide, while at pH values above 6, the T.U.D. produced undergoes hydrolysis, resulting in a remarkable reduction in yield. To prevent such a drawback, the said U.S. patent proposes maintaining the pH of the reaction solution at 2 to 6 by making unreacted thiourea present 0.5 to 1.0% in the reaction solution.

However, the method of the said U.S. patent cannot produce T.U.D. in high yield and in high purity. Because, the reaction of thiourea and hydrogen peroxide is so fast and the reaction heat is so high that a local generation of by-products is unavoidable; besides, by the generation of the by-products the decomposition of T.U.D. proceeds as time goes by, thus allowing production of a large quantity of sulfuric acid. Therefore, by merely changing the method of addition of thiourea and hydrogen peroxide and making unreacted thiourea present 0.5 to 1.0% in the reaction solution it is impossible to suppress a side reaction, nor is it possible to prevent the lowering of pH of the reaction solution. In addition, such a reduction in pH value causes production of a large quantity of disulfide. The disulfide thus produced forms a salt of low solubility with the sulfuric acid by-produced, which is incorporated into the product T.U.D. and causes its purity to deteriorate.

U.S. Pat. No. 3,355,486 proposes a method in which the reaction time of thiourea and hydrogen peroxide is kept within 7 minutes to minimize the by-production of sulfuric acid and to complete the reaction before production of sulfuric acid, and the pH of the reaction solution is maintained in the range of from 3 to 7. However, the yield of T.U.D. produced according to this method is extremely low because of an extreme short reaction time.

Furthermore, Japanese patent publication No. 17665/1970 proposes a method in which the reaction solution after completion of reaction and after separation of crystals is treated with a carbonate or hydroxide of an alkaline earth metal to remove sulfuric acid which hinders the reaction, and the reaction solution thus treated is reused as the next reaction solution whereby the T.U.D. dissolved in the reaction filtrate is recovered and the yield of T.U.D. improved.

The above method cannot prevent the by-production of sulfuric acid during reaction and does not remedy the drawbacks associated with the prior art process, that is, disulfide as a reaction by-product forms a salt with sulfuric acid, which is incorporated into the product T.U.D. and thereby deteriorates the purity of the product. The above method merely aims at improving the yield of T.U.D. by recovering the T.U.D. dissolved in the reaction filtrate. According to such method, however, an alkaline earth metal enters into the reaction solution, thus not only promoting the decomposition of hydrogen peroxide, but also causing the basicity of an alkali agent to become too high, so that the decomposition of T.U.D. as well as the neutralization of sulfuric acid which is the primary object is promoted, which causes lowering of the yield and purity of the product. This drawback is pointed out in Japanese patent public disclosure No. 62934/1975.

Consequently, in the conventional methods the yield of the object substance is 70% or so and the purity of product is also low, which is 96% or so, and it is difficult to further improve the yield and purity of product, and in many cases the results are unsatisfactory.

Thus, in the production of T.U.D. by the reaction of thiourea and hydrogen peroxide according to the prior art, it is apparent that if the reaction is carried out while maintaining the pH of the reaction solution in the range of from 2 to 7, a high purity T.U.D. can be prepared in high yield, and also it is easily inferable that this object can be attained if by-produced sulfuric acid, etc. are neutralized by adding a neutralizer or a weak acid pH buffer agent into the reaction solution.

In view of the above point, we have actually added the following alkaline neutralizers and weak acid pH buffer agents into the reaction solution and thereby made experiments as well as studies of a wide range: mono, di, or tri sodium, potassium or ammonium salt of a primary, secondary or tertiary phosphoric acid, sodium, potassium or ammonium salt of carbonic acid, sodium, potassium or ammonium salt of bicarbonic acid, caustic soda, caustic potash, and aqueous ammonia. However, they did not contribute to the improvement in yield and purity of the product T.U.D.

This is because in case an alkaline neutralizer is added, T.U.D. as the reaction product easily decomposes due to the presence of an alkali, and also because in the case of using a weak acid substance as a pH buffer agent, a large quantity of the pH buffer agent must be added in order to maintain the pH of the reaction solution in a preferred range, resulting in that the purity of the product T.U.D. deteriorates.

Thus, it became clear that merely by keeping an optimum pH range by the use of a neutralizer or a pH buffer agent it is difficult to obtain a high purity T.U.D. in high yield.

SUMMARY OF THE INVENTION

Having made studies of the functional mechanism of various chemicals in the reaction of thiourea and hydrogen peroxide, we found that if ammonium bicarbonate is added into the reaction solution, there can be obtained a unique effect which by the use of other chemicals is not obtainable.

DESCRIPTION OF THE INVENTION

We found that if ammonium bicarbonate is continuously added into the reaction solution in the reaction of thiourea and hydrogen peroxide, the production of by-products and the hydrolysis of T.U.D. are suppressed, besides such added substance does not act as an interfering substance in the manufacturing process of T.U.D., resulting in that reaction yield is remarkably improved from the conventional 70% to 85% or higher and the purity of product also improved as compared with that attained by the conventional methods.

It should be specially noted that only when ammonium bicarbonate was added, its effect was recognized, despite no effect having been recognized by the addition of sodium bicarbonate, potassium bicarbonate, potassium carbonate, sodium carbonate, and ammonium carbonate. This is probably because ammonium bicarbonate acts as a negative catalyst for the side reaction in the reaction of thiourea and hydrogen peroxide and for the hydrolysis reaction of the resulting T.U.D. But its functional mechanism is unknown.

The quantity of ammonium bicarbonate to be added somewhat differs according to reaction conditions, but usually it is continuously added so that the ratio of ammonium bicarbonate per mole of T.U.D. in the reaction solution is 0.01 to 0.2 mole. Regarding the method of addition of ammonium bicarbonate, it may be added in a separate manner, that is, thiourea, hydrogen peroxide and ammonium bicarbonate may be added separately into the reaction solution, or alternatively, ammonium bicarbonate may be dissolved in an aqueous thiourea solution and the resulting solution may be added into the reaction solution.

In the present invention, the concentration of hydrogen peroxide used in the reaction is in the range of from 20% to 70% and preferably from 35% to 65%. If hydrogen peroxide at a concentration above 70% is used, the quantity of by-products increases, while at a concentration below 35% the quantity of the reaction solution increases, which results in increase of the dissolution loss of T.U.D.

Regarding the concentration of thiourea contained in the aqueous thiourea solution which is used in the reaction, the range of from a 5% solution to a saturated aqueous solution is preferable from the standpoint of production, but a slurry consisting of a solid-liquid mixture of thiourea may also be used without any trouble. The higher the concentration of thiourea, the smaller the quantity of the reaction solution required and that of the dissolution loss, which leads to the improvement in yield. However, making the concentration higher than required would cause a local decomposition of T.U.D. during reaction and thus is not desirable.

The reaction temperature is preferably below 10° C. and as low a reaction temperature as possible is desirable to prevent a side reaction. As to the cooling method, the use of a refrigerator which is usually adopted industrially or the utilization of vacuum evaporation may be adopted.

Regarding the method of reaction between thiourea and hydrogen peroxide, the molar ratio in the reaction solution should be such that thiourea is added always in excess with respect to hydrogen peroxide. But a large excess thereof causes increase in the loss of thiourea, which is not economical. Therefore, it is desirable that the molar ratio of thiourea to hydrogen peroxide in the reaction solution be in the range of from 1.5:1 to 2:1.

A preferred method of addition of the starting chemicals is either adding hydrogen peroxide and ammonium bicarbonate solution into the required thiourea solution, or adding thiourea, hydrogen peroxide and ammonium bicarbonate solutions simultaneously into a reaction vessel. The former method can be adopted mainly in batch system, while the latter method is adoptable in batch system and also in such a continuous system as is disclosed in U.S. Pat. No. 3,355,486.

DESCRIPTION OF PREFERRED EMBODIMENTS

Preferred embodiments of the present invention are as shown below.

Ammonium bicarbonate (10 g/l) is added to an aqueous thiourea solution (concentration: 130 g/l) to prepare a mixed solution. Then, the mixed solution and hydrogen peroxide (concentration: 600 g/l) are simultaneously added into a reactor with vigorous stirring while the temperature is maintained below 10° C. As the reaction proceeds, crystals of T.U.D. are deposited to form a mixed solid-liquid phase. The deposited crystals may be separated continuously, or may be left as a mixed solid-liquid phase until the reaction is completed. Preferably, the reaction of thiourea and hydrogen peroxide is completed, then the crystals of T.U.D. are aged and thereafter filtered off. According to such an operation, it is possible to obtain T.U.D. in yields of 85% to 90% and purities of 99% or higher.

Comparative examples and working examples of the present invention are given below, but these are for illustration only and not intended to restrict the invention.

COMPARATIVE EXAMPLE 1

450 g of thiourea was added into 3 l of hot water at 40° C. and a thorough stirring was applied to allow thiourea to dissolve completely, followed by further addition of hot water to adjust the final quantity of the solution to 3.6 l (concentration: 125 g/l). The aqueous thiourea solution thus prepared was cooled and then 0.74 l of hydrogen peroxide (concentration: 50%) was added slowly at a rate such that the solution temperature was held below 10° C. Thereafter, the solution was cooled to 0° C. and stirring continued for about 30 minutes to allow crystals to be aged.

After the crystal ageing, the solid-liquid mixture at 0° C. was immediately filtered and the fractionated crystals dried at 50° C. to yield 440 g.

The purity and yield of the crystals thus obtained were 95.3% and 69%, respectively.

COMPARATIVE EXAMPLE 2

In the same manner as in Comparative Example 1, 450 g of thiourea was dissolved in 3 l of hot water at 40° C. After the thiourea had been dissolved completely, hot water was further added to prepare 3.6 l of solution at the final concentration of 125 g/l. Separately, 0.6 l of a 30 g/l solution of ammonium carbonate was prepared. Thereafter, the same reaction as in Comparative Example 1 was carried out while the ammonium carbonate solution was added simultaneously with the addition of hydrogen peroxide at a rate such that the addition of 0.6 l was completed at the time of termination of the reaction.

The purity and yield of the crystals thereby obtained were 95.7% and 64.5%, respectively.

COMPARATIVE EXAMPLE 3

T.U.D. was prepared in the same manner as in Comparative Example 2 except that a 20 g/l solution of caustic soda was used in place of ammonium carbonate.

The purity and yield of the crystals thus obtained were 96.4% and 60.2%, respectively.

COMPARATIVE EXAMPLE 4

T.U.D. was prepared in the same manner as in Comparative Example 2 except that a 75 g/l solution of mono sodium phosphate was used in place of ammonium carbonate.

The purity and yield of the crystals thus obtained were 84.2% and 65.4%, respectively.

COMPARATIVE EXAMPLE 5

The same procedure as in Comparative Example 2 was reiterated with the proviso that a 5 g/l solution of ammonium aqueous solution was used in place of ammonium carbonate, to prepare T.U.D.

The purity and yield of the crystals thus obtained were 88.3% and 69.3%, respectively.

EXAMPLE 1

In the same way as in the above Comparative Examples, 450 g of thiourea was dissolved in 3 l of hot water at 40° C. After the thiourea had been dissolved completely, there was prepared 3.6 l of solution at the final concentration of 125 g/l. Separately, 0.6 l of a 50 g/l solution of ammonium bicarbonate was prepared. The aqueous thiourea solution was cooled and then 0.74 l of hydrogen peroxide was added slowly while the solution temperature was maintained below 10° C. Also, addition of the ammonium bicarbonate solution was started simultaneously with the addition of hydrogen peroxide so that the ratio of ammonium bicarbonate per mole of T.U.D. in the reaction solution was 0.08 mole. Thereafter, the solution was cooled to 0° C. and stirring continued for about 30 minutes to allow crystals to be aged.

After the crystal ageing, the crystals were filtered off and then dried at 50° C. to yield 531 g of the object substance.

The purity and yield of the crystals thus obtained were 99.2% and 87%, respectively.

EXAMPLE 2

The same procedure as in Example 1 was repeated with the proviso that in place of 3.6 l of an aqueous thiourea solution there was used a mixed thiourea-ammonium bicarbonate solution in which was dissolved 30 g of ammonium bicarbonate.

The purity and yield of the crystals thus obtained were 99.4% and 88.4%, respectively.

We claim:

1. A process for preparing thiourea dioxide characterized in that in the production of thiourea dioxide by the reaction of thiourea and hydrogen peroxide in an aqueous solvent, sufficient ammonium bicarbonate is added continuously to the reaction solution so that the ratio of ammonium bicarbonate per mole of thiourea dioxide in the reaction solution is in the range of from 0.01 to 0.2 mole.

2. A process according to claim 1, in which the concentration of hydrogen peroxide used in the reaction is in the range of from 20% to 70%.

3. A process according to claim 1, in which the reaction of thiourea and hydrogen peroxide is carried out at a temperature below 10° C.

4. A process according to claim 1, in which the molar ratio of thiourea to hydrogen peroxide in the reaction solution is in the range of from 1.5:1 to 2:1.

5. The process of claim 2, in which said concentration is in the range of from 35% to 65%.

* * * * *